United States Patent [19]

Dekura

[11] Patent Number: 4,898,683
[45] Date of Patent: Feb. 6, 1990

[54] SYNTHETIC LUBRICANTS

[76] Inventor: Takateru Dekura, No. 1-3, Sasame-cho, Kamakura-shi, Kanagawa-ken, Japan

[21] Appl. No.: 280,357

[22] Filed: Dec. 6, 1988

[30] Foreign Application Priority Data

Aug. 23, 1988 [JP] Japan .................................. 62-209774

[51] Int. Cl.$^4$ .......................................... C10M 137/16
[52] U.S. Cl. ......................................... 252/51; 252/50; 252/58; 558/80
[58] Field of Search ................ 252/50, 51, 58, 51.5 R; 555/80

[56] References Cited

U.S. PATENT DOCUMENTS

| | | | |
|---|---|---|---|
| 2,586,312 | 2/1948 | Dishon | 558/80 |
| 2,876,247 | 3/1959 | Rätz | 558/80 |
| 3,206,494 | 9/1965 | Lund | 558/80 |
| 3,888,800 | 6/1975 | Allock | 558/80 |
| 3,891,448 | 6/1975 | Braxton | 558/80 |
| 3,894,876 | 7/1975 | Wolf | 558/80 |
| 4,192,830 | 3/1980 | Wolf | 558/80 X |

*Primary Examiner*—William R. Dixon, Jr.
*Assistant Examiner*—James M. Hunter, Jr.
*Attorney, Agent, or Firm*—Fleit, Jacobson, Cohn, Price, Holman & Stern

[57] ABSTRACT

Synthetic lubricants of the formula:

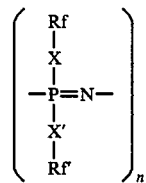

wherein, n is from 3 to 10; X and X' are NH or $NH_2$, with the proviso that X and X' are not both $NH_2$; Rf and Rf' are $Y(C_3F_6O)_{\overline{l-1}}$—CFZCO, $Y(C_3F_6O)_{\overline{l}}$—$(CF_2O)_{\overline{m}}$—CFZCO, $Y(C_2F_4O)_{\overline{l}}$—$(CF_2O)_{\overline{m}}$—CFZO, $Y(CF_2)_{\overline{l-1}}$—CO, $Y(CF_2)_{\overline{l-1}}$—$CH_2$CO, and $Y(CF_2)_{\overline{l-1}}$—$CH_2CH_2$CO, wherein l>m, l is an integer from 3 to 150, m is an integer from 1 to 50, Y is H—, F—, $CF_3$—, $C_2F_5$—, $C_3F_7$—, $CF_3O$—, $C_2F_5O$—, or $C_3F_7O$—, and Z is F—, $CF_3$—, or $C_2F_5$—. The synthetic lubricants have enhanced adsorption on metals, graphite, amorphous carbon, and other inorganic materials, have improved corrosion protection and load resistance properties, a favorable lubricating behavior, and low combustibility.

3 Claims, No Drawings

SYNTHETIC LUBRICANTS

BACKGROUND OF THE INVENTION:

(1) Field of the Invention

The present invention relates to fluorine-containing compounds having phosphonitrile amides as substituents. These are synthetic lubricants having a solid or pasty consistency at normal temperatures and obtained by introducing different types of fluorine-containing compounds as well as synthetic lubricants which are liquids at normal temperatures and obtained by introducing identical or different types of fluorine-containing compounds.

The lubricants in accordance with the invention may take the form of solid and liquid lubricants and are capable of being used for the lubrication and corrosion protection of the contact surfaces of machinery or equipment with moving parts, in which applications they will provide a superior effect.

(2) Description of the Prior Art

Polychlorophosphonitrile, a compound consisting of chlorine, phosphorus, and nitrogen atoms, can be obtained in high yield by reacting phosphorus pentachloride with ammonium chloride, and from these, organic phosphonitriles are obtained by bonding them with organic compounds having a straight chain or an aromatic ring structure, such organic phosphonitriles being used as flame retardants, synthetic rubbers, and synthetic lubricants.

Organic straight-chained polymeric phosphonitriles that are used as synthetic rubbers and trimeric, tetrameric and oligomeric phosphonitriles with organic ring structures in the molecule are known from U.S. Pat. Nos. 2,109,490, 3,131,207, 4,018,967, and 4,613,548 and have also been described in the literature in the A.S.L.E. Transactions 7, 389–397 (1964), and applications thereof have been described in the Japanese Patent Provisional Publication Nos. 252292/1986, 260088/1986, and 250098/1987.

These are given as being compounds obtained by reacting trimeric and tetrameric polychlorophosphonitriles with alkoxy-substituted phosphonitriles and an alkyl or aryl amine.

Many types of lubricants for electronic equipment used in recent years, for example, surface lubricants for magnetic recording devices as well as lubricants for connectors and contactors, employ a variety of inorganic and organic substances, and their use has demonstrated that it is difficult to extend the surface life of the equipment solely by virtue of the lubricants' wetting power.

Moreover, perfluoroalkyl polyethers are being used as oil and grease lubricants for bearings. Their problem, however, is that due to the lack of adhesion onto the metal surface they lead to an inferior corrosion resistance and to a reduced service life of the bearing, so that means are being sought to resolve these difficulties.

Fluorinated lubricants are being widely used in applications requiring a chemical inertness and heat resistance, and research and development has been directed toward the achievement of stable compounds rather than compounds resistant to extremely severe application conditions.

The principal application fields are therefore limited to the semiconductor industry using non-combustible corrosive gases with a low vapor pressure, for bearings, plant conveyors and chains as well as furnace peripherals liable to operate at elevated temperatures.

The superior qualities of fluorinated lubricants, however, can be recognized from the fact that these compounds are being applied to a wide range of applications in factory automation, industrial robots, computer equipment, and electric household appliances.

These lubricants have to meet a broad range of requirements when used in such equipment, and experience so far has shown that fluorinated lubricants are in many instances not capable of fulfilling these requirements.

Perfluorinated alkylpolyether lubricants, that is, compounds in which all hydrogen atoms have been replaced by fluorine, do not posses satisfactory load carrying capacity in the low-molecular range but exhibit a satisfactory wettability and a low surface tension in the high-molecular range. Yet, due to their poor adhesion to metals, their use would give rise to lubricant migration and loss of lubrication performance if and when used for the lubrication of equipment rotating at high speed.

If the compounds are rendered too stable, it will thus be found that the adsorption on to metals will be weakened and that though exhibiting a satisfactory lubricating effect in the initial period, their effectiveness as lubricants for sliding away equipment tends to diminish, if used for a prolonged period of time, due to lubricant depletion consequent to lubricant migration.

For this reason, it is essential to enhance lubricant adsorption and improve the wear resistance of lubricants even if this implies a certain trade-off by sacrificing their stability to a certain extent, as may be required by some applications.

SUMMARY OF THE INVENTION

The aim of the present invention, as the result of the most dedicated research on the problems referred to the above, is therefore to provide synthetic lubricants with an enhanced adsorption on metals, graphite, amorphous carbon, and other inorganic materials, improved corrosion inhibition and load resistance properties, a favorable lubricating behavior, and low combustibility.

DESCRIPTION OF THE PREFERRED EMBODIMENTS

The present invention will be explained in detail hereinunder.

The compounds according to this invention have the general structure of phosphonitriles subjected to amidation and having polar groups between the radicals which may consist of fluoroalkylcarbonyl, fluoroalkylmethyl or ethylcarbonyl, polyperfluorooxyalkyleneperfluoropropionyl, and/or a copolymerized polyperfluorooxyalkylene- fluorooxyalkylene-fluoroalkylcarbonyl chain.

The novel compounds referred to above are lubicants whose molecular structure can generally be represented by formula (I), whereby it is desirable that Rf and Rf' should have a molecular weight of 200–15,000.

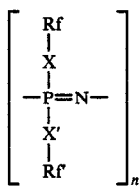

(I)

In this formula, n may be considered as having a value in the range from 3 to 10 and X, X' may represent either NH or NH and Rf and Rf' may be one or two or more of the radicals selected from the group consisting of the following: Rf and Rf'

| Y(C$_3$F$_6$O)$_l$ | | CFZCO |
| Y(C$_3$F$_6$O)$_l$ | (CF$_2$O)$_m$ | CFZCO |
| Y(C$_2$F$_4$O)$_l$ | (CF$_2$O)$_m$ | CFZCO |
| Y(CF$_2$)$_{l-1}$ | | CO |
| Y(CF$_2$)$_{l-1}$ | | CH$_2$CO |
| Y(CF$_2$)$_{L-1}$ | | CH$_2$CH$_2$CO | where l is an integer having a value between 3 and 150, and m is an integer ranging from 1 to 50, and where Y may be H—, F—, CF$_3$—, C$_2$F$_5$—, C$_3$F$_7$—, CF$_3$O—, or C$_3$F$_O$—, and Z may be F—, CF$_3$—, or C$_2$F$_5$—, respectively.

That is, in a synthetic lubricant consisting of a fluorine-containing phosphonitrile amide represented by the general formula (1) above, if either X or X' is NH$_2$ and Rf or Rf' is absent.

The following is a more detailed description of the present invention.

The compounds including the synthetic lubricants according to the present invention are phosphonitrile derivatives having the structure as shown in formula (I) hereinabove.

In the compounds with the structure shown in formula (I) Rf and Rf' may be identical or different radicals, with the function of the radicals Rf and Rf' being that of determining the lubricant's viscosity, viscosity/-temperature behavior, and lubricating properties.

Perfluorooxyalkyleneperfluoropropionyl compounds with a low molecular weight (m.w. 1,500 or less) have a satisfactory low-temperature behavior but exhibit an inferior load carrying capacity resistance.

By contrast, however, perfluorooxyalkyleneperfluoropropionyl compounds with a high molecular weight (m.w. 2,500 or more) have a high viscosity and thus a poor viscosity behavior at low temperatures but exhibit a superior load carrying capacity resistance.

If Rf and Rf' are fluoroalkylcarbonyl and fluoroalkylalkylcarbonyl radicals, the lubricant compounds tend to be solid and usually have characteristics that fall within the scope of solid lubricants.

If the lubricant compounds, however, are mixtures of polyperfluorooxyalkyleneperfluoropropionyl, copolymerized polyperfluorooxyalkylenefluorooxymethylene derived carbonyl and fluoroalkylcarbonyl, and fluoralkylalkylcarbonyl, it is possible to adjust the lubricant consistency from being liquid to being pasty at normal temperatures in accordance with the composition of this mixture.

Consequently, it is possible to control the effectiveness of the lubricants to suit their different applications in machinery and equipment by engineering the appropriate characteristics such as a high melting point, a high viscosity, and a low pour point.

Effect

Fluorine-containing phosphonitrile amides derived from phosphonitrile amide exhibit satisfactory lubricating properties with respect to inorganic and organic materials and are characterized in that they impart corrosion inhibition properties to the metal surface and possess fire resistant properties and an outstanding wetting power due to their low surface tension.

EXAMPLES

Examples will be shown in the following.

The following are some practical examples of the present invention which shall, however, not be limited by, or restricted to, these examples.

Amide derivatives of phosphonitrile are obtained, in one example, by reacting polychlorophosphonitrile and liquid ammonium under elevated pressure conditions in an autoclave and by subsequently evacuating the ammonium gas and expelling the residual ammonium gas completely in a low-pressure (vacuum) desiccator, while the by-product ammonium chloride formed in the reaction is eliminated by recrystallization with alcohol.

The compounds generally represented by the above formula (1) can be synthesized by the procedures given hereinafter by way of example.

EXAMPLE 1

11 g (0.108 mol) of triethylamine were added to a dispersant which is obtained by adding 4.2 g (0.018 mol) of hexaaminocyclotriphosphonitrile (having the chemical formula [N=P(NH$_2$)$_2$]$_3$) to a mixture of 100 ml of dehydrated refined trichlorotrifluoroethane and 50 ml of N,N'-dimethylformamide into a four-neck 500 ml flask equipped with a stirrer, thermometer, reflux cooler, and dripping funnel and the mixture thus obtained was kept at a constant temperature of 5° C. while homogenizing it by stirring.

While homogenizing the solution by stirring, 200 g (0.108 mol) of perfluoroalkylpolyetherperfluoropropionylchloride [(average molecular weight 1850, as determined by nuclear magnetic resonance spectroscopy) chemical formula: F(C$_3$F$_6$O)$_l$—C$_2$F$_4$COCl, where l has a value of approximately 10, acid number 32 mgKOH/g, viscosity at 38° C.:90 centistokes] were drip-fed with a dripping funnel for one hour, into 200 ml of refined trichlorotrifluoroethane, whereupon the reaction was allowed to take place by stirring the mixture on a reflux stirrer for 48 hours at a temperature of 5°–10° C.

After the reaction had reached completion and after the unreacted solids had been filtered off and the trichlorotrifluoroethane distilled off at 50° C., the reaction mixture was transferred into a separating funnel and was allowed to stand, following the addition of a small amount of 0.25N hydrochloric acid and 100 ml of methyl alcohol, when the bottom layer was drawn off.

The bottom layer thus withdrawn was washed with distilled water to purify for at least three or four times until no color change was detectable in the presence of methyl orange indicator. After this, the solvent was distilled off under a vacuum, and the unreacted perfluoroalkylpolyetherperfluoropropionic acid was distilled under a vacuum drawn to 0.03 mm Hg at a temperature of 134°–137° C. to obtain the liquid reaction product in 78% yield. Determination of the viscosity at 40° C. gave a value of 105 centistokes and determination of the acid number produced a value of 0.3 mg KOH/g.

Infrared spectral analysis (performed with an IR spectrometer model IR810 manufactured by Nihon Bunko Kogyo Kabushiki Kaisha) showed that the 1680–1740 cm$^{-1}$ and 3350 cm$^{-1}$ absorption bands characteristic of amide absorption were present while there was no clear evidence of the 1262 cm$^{-1}$ absorption for the stretching vibration of the P=N bond and the 128 cm1)absorption band characteristic of the C-F bond. An absorption band at 540 cm$^{-1}$, attributable to the P-N bond was present.

Elemental analysis performed with a YANACO CHN coder MT3 model manufactured by Kabushiki Kaisha Yanagimoto Seisakusho revealed 21.0% C and 1.0% N as compared with theoretical values of 21.4% C and 1.1% N. In view of the virtually complete agreement between the analysis results and the theoretical values, it was concluded that the product formed in the above reaction procedure had the formula (1):

  (1)

EXAMPLE 2

31 g (0.306 mol) of triethylamine were added to a dispersant which is obtained by adding 12 g (0.052 mol) of hexaaminocyclotriphosphonitrile (having the chemical formula [N=P(NH$_2$)$_2$]$_3$) to 50 ml of dehydrated N,N'-dimethylformamide, into a four-neck 500 ml flask similar to example 1, and the mixture thus obtained was kept at a constant temperature of 5° C. while homogenizing it by stirring.

While homogenizing the solution by stirring, 150 g (0.302 mol) of perfluoroalkylmethylcarbonylchloride [chemical formula: C$_8$F$_{17}$CH$_2$COCl (molecular weight 496.5, melting point: 29° C., boiling point: 81°–82° C./11 mm Hg)]were drip-fed, with a dripping funnel for one hour, into 200 ml of refined N-methyl 2-pyrrolidone, whereupon the reaction was allowed to take place by stirring the mixture with a stirrer for 48 hours at a temperature of 5°–10° C.

After the reaction had reached completion, addition of 0.25N aqueous hydrochloric acid was made and the reaction products in the bottom layer were withdrawn into a dripping funnel and washed to wash out the unreacted products with subsequent filtration.

The filtered reaction product was then washed with distilled water to purify for at least four or five times until no color change was detectable in the presence of methyl orange indicator. After drying, a white solid product was obtained.

This solution was then distilled in a temperature range of 115°–120° C./0.5 mm Hg by gradually reducing the pressure to distill off the unreacted perfluorooctylmethylcarboxylic acid (melting point: 83° C.) so as to obtain the solid reaction product having a melting point of 230°–240° C. and an acid number of 0.5 mg KOH/g in 81% yield. Infrared spectral analysis showed no evidence of an absorption band at 1720 cm$^{-1}$ and revealed clear peaks at 1690 cm$^{-1}$ and 3100–3400 cm$^{-1}$ characteristic of the substituted amides, with absorption bands for the P-N-P (SY) bond vibration at 780 cm$^{-1}$ and 950 cm$^{-1}$ and an absorption band at 540 cm$^{-1}$, attributable to the P-N bond.

Elemental analysis performed in such a manner as in example 1 revealed 24.5% C and 4.3% N as compared with theoretical values of 24.0% C and 4.2% N. In view of the virtually complete agreement between the analysis results and the theoretical values, it was concluded that the product formed in the above reaction procedure had the formula (2):

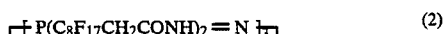  (2)

EXAMPLE 3

20.5 g (0.202 mol) of triethylamine were added to a dispersant, obtained by adding 8 g (0.034 mol) of hexaaminocyclotriphosphonitrile to a mixture of 50ml of dehydrated refined trichlorotrifluoroethane and 100 ml of N,N'-dimethylformamide, into a four-neck 500 ml flask similar to example 1, and the mixture thus obtained was kept at a constant temperature of 0° C.–5° C. while homogenizing it by stirring.

While homogenizing the solution by stirring, a mixture of 100 g (0.1 mol) of perfluoroalkylpolyetherperfluoropropionyl chloride [chemical formula: F(C$_3$F$_6$O)$_l$—C$_2$F$_4$COCl, where l has a value of approximately 5 (average molecular weight 1000, as determined by nuclear magnetic resonance spectroscopy, viscosity at 38° C.:44 centistokes, acid number 32 mgKOH/g] dissolved in 100 ml of trichlorotrifluoroethane and 50 g (0.1 mol) of perfluoroctylmethylcarbonyl chloride [chemical formula: C$_8$F$_{17}$CH$_2$COCl (molecular weight 496.5, melting point: 29° C., boiling point: 81°–82° C./11 mm Hg)] dissolved in 100 ml of N-methyl-2-pyrrolidone were dripped from a dripping funnel for one hour at a temperature of 0° C.–5° C., whereupon the reaction was allowed to take place by stirring the mixture on a reflux stirrer for 48 hours at a temperature of 5°–10° C.

After the reaction had reached completion, the unreacted solids were filtered off and the trichlorotrifluoroethane was distilled off, whereupon the reaction product was transferred into a separating funnel and after addition of 0.25 N hydrochloric acid, the bottom layer was withdrawn after sedimentation.

The bottom layer thus withdrawn was then washed with distilled water to purify for at least four or five times until no color change was detectable in the presence of methyl orange indicator or no finely disperse clouding of a silver nitrate solution was detectable. After this, the solvent was removed by vacuum distillation, and the unreacted perfluoropropionic acid and perfluorooctylmethylcarboxylic acid were removed by renewed vacuum distillation at a low pressure of 0.03 mm Hg and at a temperature ranging from 85°–100° C., when the product, having a liquid consistency at normal temperatures, was obtained in 75% yield.

Determination of the viscosity at 40° C. gave a value of 135 centistokes and determination of the acid number resulted in a value of 0.4 mg KOH/g.

Infrared spectral analysis showed a shift of the 1780 cm$^{-1}$ absorption peak to 1680 cm$^{-1}$–1700 cm$^{-1}$ and revealed a large peak at 3350 cm$^{-1}$ characteristic of the amide bond.

Elemental analysis performed in such a manner as in example 1 revealed 23.0% C and 3.0% N as compared with theoretical values of 22.2% C and 2.8% N. In view of the virtually complete agreement between the analysis results and the theoretical values, it was concluded that the product formed in the above reaction procedure had the formula (3):

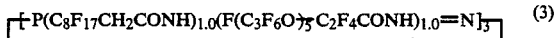

$$[P(C_8F_{17}CH_2CONH)_{1.0}(F(C_3F_6O)_5C_2F_4CONH)_{1.0}=N]_3 \quad (3)$$

EXAMPLE 4

5 g (0.049 mol) of triethylamine were added to a dispersant, obtained by adding 2 g (0.008 mol) of hexaaminocyclotriphosphonitrile to 50 ml of dehydrated refined trichlorotrifluoroethane, into a four-neck 500 ml flask similar to example 1, and the mixture thus obtained was kept at a constant temperature of 0° C.–5° C. while homogenizing it by stirring.

While homogenizing the solution by stirring, 200 g (0.047 mol) of perfluoroalkylpolyetherperfluoropropionyl-chloride [chemical formula: $F(C_3F_6O)_l\text{—}C_2F_4COCl$, where l has a value of approximately 24 (average molecular weight 4200, as determined by nuclear magnetic resonance spectroscopy, viscosity at 38° C.: 320 centistokes, acid number 12 mgKOH/g] were drip-fed, for one hour at a temperature of 0° C.–5° C. by means of a dripping funnel, into 200 ml of refined trichlorotrifluoroethane, whereupon the reaction was allowed to take place by stirring the mixture on a reflux stirrer for 48 hours at a temperature of 5°–10° C.

After the reaction had reached completion, the unreacted solids were filtered off and the trichlorotrifluoroethane was distilled off at a temperature of 50° C., whereupon the reaction mixture was transferred into a separating funnel and after addition of a small amount 0.25 N hydrochloric acid and 100 ml of methyl alcohol, the bottom layer was withdrawn after sedimentation.

The bottom liquid thus withdrawn was then washed with distilled water to purify for at least three or four times until no color change was detectable in the presence of methyl orange indicator.

After the further addition of a small amount of sodium bicarbonate and 100 ml methyl alcohol to convert the unreacted carboxylic acid to the corresponding salt, the solution was washed two or three times with 100ml methyl alcohol to remove the salt, with subsequent washing with distilled water to neutralize. After this, the liquid product was obtained in 70% yield.

Determination of the viscosity at 40° C. gave a value of 450 centistokes and determination of the acid number resulted in a value of 0.7 mg KOH/g.

Infrared spectral analysis showed a very minor absorption band at 1780 cm$^{-1}$ and revealed clear absorption peaks at 1680 cm$^{-1}$–1740 cm$^{-1}$ and at 3350 cm$^{-1}$ characteristic of the amide bond as well as an absorption band at 540–560 cm$^{-1}$ attributable to the P-N bond.

Elemental analysis performed in such a manner as in example 1 revealed 22.5% C and 0.6% N as compared with theoretical values of 21.6% C and 0.5% N. In view of the virtually complete agreement between the analysis results and the theoretical values, it was concluded that the product formed in the above reaction procedure had the formula (4):

$$[P(F(C_3F_6O)_{24}\text{–}C_2F_4CONH)_2=N]_3 \quad (4)$$

Table 1 gives the characteristics of the synthetic lubricant compounds with a corrosion-protection effect obtained in the above examples.

TABLE 1

| | Example 1 | Example 2 | Example 3 | Example 4 | Perfluoro polyether C (Note 1) |
|---|---|---|---|---|---|
| Appearance (Room Temperature) | Clear yellowish Liquid | Yellowish solid | Yellowish liquid | Yellowish liquid | Clear colorless liquid |
| Flash Point ASTM D 92 | Nonflammable | — | Nonflammable | | |
| Viscosity 40° C. | 105 | Melting point 230–240° C. | 135 | 450 | 240 |
| Viscosity 100° C. ASTM D 445 | 10.5 | | 11.3 | 28.0 | 26.0 |
| Viscosity Index ASTM D 2270 | 77.6 | — | 56.6 | 86.7 | 122 |
| Strong Acid No. ASTM D 974 | 0.3 | 0.5 | 0.4 | 0.7 | 0.0 |
| Pour Point, °C. ASTM D 92 | −20° C. | — | −10.5 | −15.0 | −35.0 |
| Wear Preventive Characteristic (Four-Ball method) | | | | | |
| Mean Hertz Load, kg | 85 | — | 95 | 90 | 98 |
| Incipient Seizure, kg | 220 | | 220 | 250 | 200 |
| Weld Point, kg ASTM D 2783 | 300 | | 320 | 350 | 398 |
| Test for Rust Protection in the Humidity Cabinet ASTM D 1748 | 300 hrs No rust | 300 hrs No rust (Note 2) | 300 hrs No rust | 300 hrs No rust | 30 min. Rust |

Note 1:
Perfluoropolyether C manufactured by Dupont U.S.A. under the tradename Krytox 143AC (average molecular weight: 6,250) Structural formula:

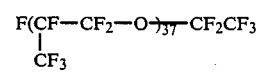

$$F(CF\text{—}CF_2\text{—}O)_{37}\text{—}CF_2CF_3$$
$$\phantom{F(}|$$
$$\phantom{F(}CF_3$$

Note 2:
Uniformly dispersed at 10% in perfluoropolyether C (grain diameter 300 mesh)

The present invention thus provides novel substances whose effectiveness as lubricants has become clear from the description hereinabove.

The use of these compounds ensures superior lubricants in terms of their adsorption on metal surfaces, their anti-corrosion action, and their lubricating properties under load conditions.

In addition, these lubricants are distinguished by non-flammability under handling conditions and their safety in use.

If these compounds are used either on their own or in combination with perfluoropolyether oils, they will therefore provide a very favorable lubricating action and be ideally suited when used for the lubrication of various types of equipment, magnetic recording devices, connectors, and the like.

Furthermore, if these compounds are combined with perfluoropolyether to produce a perfluoropolyether type grease, it is possible to upgrade the adhesion of the perfluoropolyether grease to the metal surface.

If these compounds are applied to the contact surfaces of all kind of rotating equipment or any kind of equipment with moving parts, they will exhibit a very favorable lubricating action for a long time.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. Synthetic lubricant obtained by amidation of phosphonitrilic acid by way of nucleophilic substitution, said synthetic lubricant having the formula:

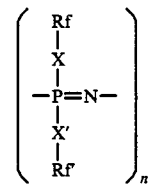

wherein, n is from 3 to 10; X and X' are each NH or $NH_2$, with the proviso that X and X' are not both $NH_2$; Rf and Rf' are each a member selected from the group consisting of $Y(C_3F_6O)_{\overline{l}}CFZCO$, $Y(C_3F_6O)_{\overline{l}}(CF_2O)_{\overline{m}}CFZCO$, $Y(C_2F_4O)_{\overline{l}}(CF_2O)_{\overline{m}}CFZCO$, $Y(CF_2)_{\overline{l-1}}CO$, $Y(CF_2)_{\overline{l-1}}CH_2CO$, and $Y(CF_2)_{\overline{l-1}}CH_2CH_2CO$, wherein $1 < m$, l is an integer from 3 to 150, m is an integer from 1 to 50, Y is H—, $CF_3$—, or $C_2F_5$—; and wherein $CF_3O$—, $C_2F_5O$—, or $C_3F_7O$—, and Z is F—, is F—, $CF_3$—, or $C_2F_5$—; and wherein when X or X' is $NH_2$, Rf or Rf' respectively, is absent.

2. Synthetic lubricant according to claim 1, wherein Rf and Rf' are each a member selected from the group consisting of $Y(C_3F_6O)_{\overline{l}}CFZCO$, $Y(C_3F_6O)_{\overline{l}}(CF_2O)_{\overline{m}}CFZCO$, and $Y(C_2F_4O)_{\overline{l}}(CF_2O)_{\overline{m}}CFZCO$.

3. Synthetic lubricant according to claim 1, wherein Rf and Rf' are each a member selected from the group consisting of $Y(CF_2)_{\overline{l-1}}CO$, $Y(CF_2)_{\overline{l-1}}CH_2CO$, and $Y(CF_2)_{\overline{l-1}}CH_2CH_2CO$, and l is an integer from 3 to 30.

* * * * *